United States Patent [19]

London

[11] 4,301,552
[45] Nov. 24, 1981

[54] ENDOPROSTHETIC JOINT DEVICE

[75] Inventor: James T. London, Rancho Palos Verdes, Calif.

[73] Assignee: Wright Manufacturing Company, Arlington, Tenn.

[21] Appl. No.: 102,145

[22] Filed: Dec. 10, 1979

Related U.S. Application Data

[63] Continuation of Ser. No. 799,083, May 20, 1977, abandoned.

[51] Int. Cl.³ .................................................. A61F 1/24
[52] U.S. Cl. ........................................ 3/1.91; 3/1.911; 128/92. C
[58] Field of Search ............................... 3/1.9–1.911; 128/92. C

[56] References Cited

U.S. PATENT DOCUMENTS

| | | | |
|---|---|---|---|
| 3,798,679 | 3/1974 | Ewald | 3/1.91 X |
| 3,872,519 | 3/1975 | Giannestras et al. | 3/1.91 |
| 3,878,566 | 4/1975 | Bechtol | 3/1.91 |
| 3,886,599 | 6/1975 | Schlein | 3/1.91 |
| 3,919,725 | 11/1975 | Swanson et al. | 3/1.91 |
| 3,946,445 | 3/1976 | Bentley et al. | 3/1.91 |
| 4,008,495 | 2/1977 | Cavendish et al. | 3/1.91 |
| 4,057,858 | 11/1977 | Helfet | 3/1.91 |

Primary Examiner—Ronald L. Frinks
Attorney, Agent, or Firm—Scrivener, Clarke, Scrivener and Johnson

[57] ABSTRACT

The preferred endoprosthetic joint herein described is an elbow prosthesis of hingeless form comprising (1) a humeral component having an internal fixation surface means, and an external sellar-shaped, bearing surface and (2) an ulnar component having an internal sellar-shaped bearing surface complementary to that of the humeral component and external fixation surfaces, the bearing surfaces of the humeral and ulnar components being in rotatably sliding engagement when implanted and having throughout their respective lengths transversely curved complex concave and convex configurations which are complementary to each other. The form of endoprosthesis herein described may also be utilized as a knee, ankle and wrist joint.

5 Claims, 8 Drawing Figures

ENDOPROSTHETIC JOINT DEVICE

Relation to Other Cases

This application is a continuation of my co-pending application Ser. No. 799,083, filed May 20, 1977, for Endoprosthetic Elbow Joint Device, now abandoned.

BACKGROUND OF THE INVENTION

Arthroplasty (surgical reformation) of the elbow joint is of major interest at the present time and has been generated by several factors:

(1) Resection and interposition arthroplasty of the elbow have failed to predictably relieve pain and provide the necessary motion and stability;

(2) Arthrodesis of the elbow is a disabling procedure. Arthrodesis compromises the ability to position the hand in space. Regardless of the position selected for arthrodesis, many of the functional skills of the upper extremity are sacrificed.

(3) The initial types of total elbow prostheses have an unacceptable incidence of complications. Clinical trials with existing designs (stem-fixed, hinged prostheses) have shown a marked tendency toward loosening of the prosthetic components. Souter reported that 17 of 25 Dee prostheses (68%) loosened with a follow-up from 14–40 months. Most reports also contain a significant incidence of other complications including skin sloughs, wound breakdown, fractures, infections, and nerve palsies. These complications have been attributed to the constrained hinge design of these prostheses and to the bulk of the prostheses. There has recently been reported a replacement prosthesis requiring the excision of the trochlea. The prosthesis itself is of biconical bearing surface design, the ends of which are fixed into the humeral epicondyles.

This design has certain potential drawbacks. Among these are, firstly, replacement prostheses, in general, have an increased incidence of complications as compared to resurfacing procedures. Secondly, the biconical design does not permit side to side play under varus-valgus stress in the joint, and such stress will contribute to loosening of the anchoring points of the prosthesis. Thirdly, substantial bone resection is required and, in the event that arthrodesis of the joint is later desired, this procedure would be difficult. Fourthly, the lateral stability of the joint is impaired because the radial head is excised. Fifth, the articulating surface of revolution between the humeral and ulnar components of this prosthesis is limited.

There has also been recently reported an elbow prosthesis in which the humeral and ulnar components have limited articulation over a longitudinally convex, circular (i.e., partly cylindrical) bearing surface. This cylindrical design does not prevent lateral (i.e., side to side) slippage under varus-valgus stress imposed on the prosthesis. Further, the articular bearing surface of the ulnar component is substantially less than the 175°–180° bearing surface of the normal ulna.

It is a major objective of this invention to overcome the disadvantages of the prior art devices as well as those of the structure first described above and to attempt to attain the ideal prosthesis design for an elbow joint. The ideal prosthesis for the elbow joint should have rotatably articulating bearing surfaces of 175°–180° to simulate the normal elbow flexion and extension characteristics, should have a means to efficiently resist side to side movement under varus-valgus stress imposed on the elbow joint and should also be designed to provide improved resistance to compressive axial loading, and should avoid bone resection to the greatest possible extent. The invention herein is designed with the foregoing as primary objectives. Other advantages of the design of this invention will become apparent from the summary and description hereinafter set forth.

BRIEF SUMMARY OF THE INVENTION

The endoprosthetic elbow joint device of this invention has humeral and ulnar components which are not linked or hinged and which are relatively slidingly rotatable about and along cooperating and complementary bearing surfaces. The humeral component is designed as a capping or resurfacing member for both the trochlear surface, and about $\frac{1}{3}$ of the surface of the capitellum, of the distal end of the humerus. The humeral component is elongated and has inner fixation surfaces defined by a longitudinally extending slot; the humeral component is further provided with an outer bearing surface in the form of a convexly arcuate surface of approximately 200° extent. The lateral ends of the arcuate bearing surface are provided with proximally and posteriorly converging end surfaces for better anatomical fit. Throughout the length of the outer bearing surface of the humeral component, a substantially uniform transverse shape is provided comprising a longitudinally extending centrally located concave groove of curved transverse configuration bordered on each side by convexly curved longitudinally extending ridges.

The ulnar component has rectangularly related fixation surfaces for implantation in resected ulnar bone and an internal, arcuate, concave bearing surface extending through an arc of approximately 175°–180°, said internal bearing surface having throughout its length, a uniform transverse shape formed by a longitudinally extending centrally located convex ridge of curved transverse configuration bordered on both sides by concave longitudinally extending grooves of curved transverse configuration. The dimensions and configurations of the ridges and grooves of the bearing surfaces of the humeral and ulnar components are complementary with each other and are such that the bearing surfaces closely interfit throughout the entire range of their relative movement.

The form of endoprostheses herein described for use as an elbow joint may also be utilized as an endoprosthesis for a knee, ankle and wrist joint.

DESCRIPTION OF THE INVENTION

Figure 1:
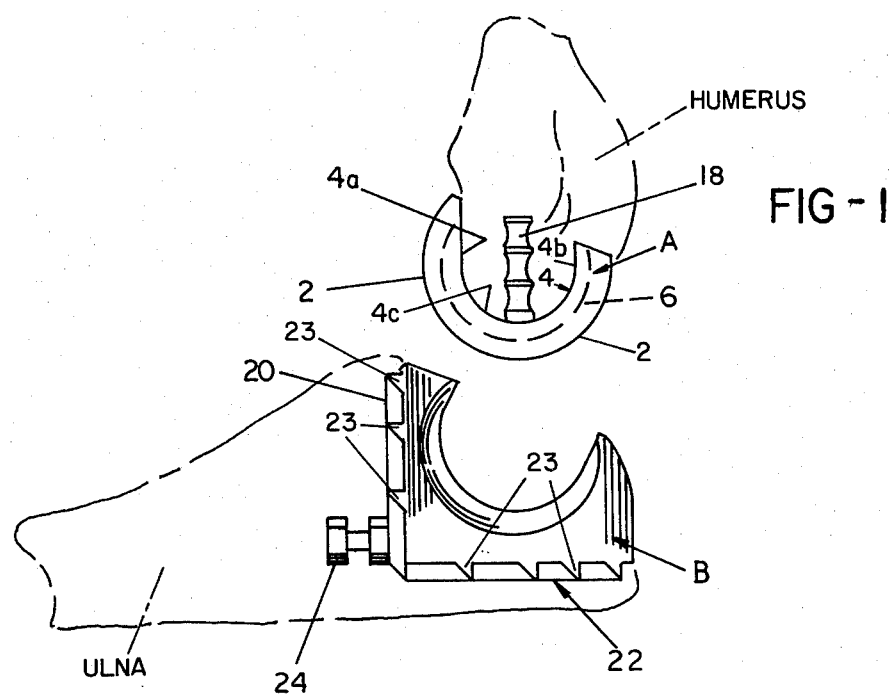
FIG. 1 shows the human humerus and ulna in medial, i.e., side elevational, view with the components of the prosthesis of the present invention implanted and in their intended operative relation.
Figure 1A:
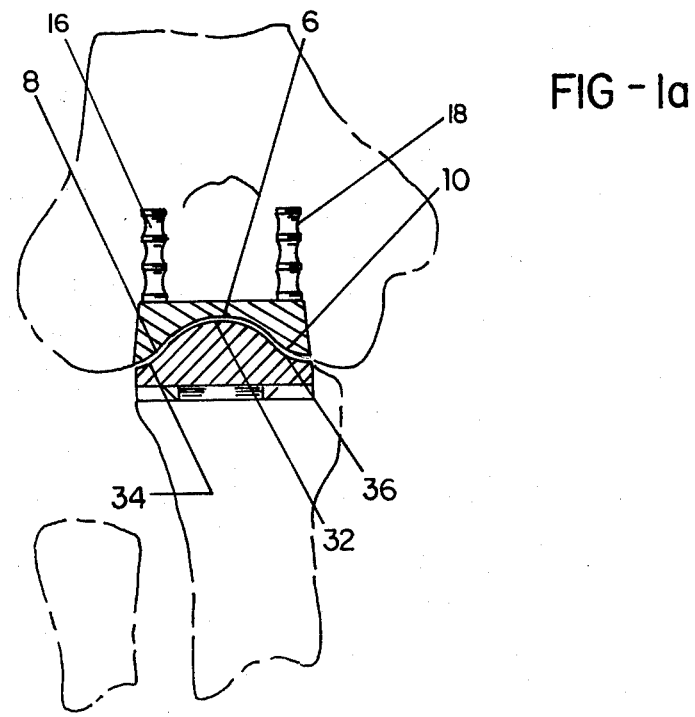
FIG. 1a is an anterior view of the implanted prosthesis.
Figure 2:
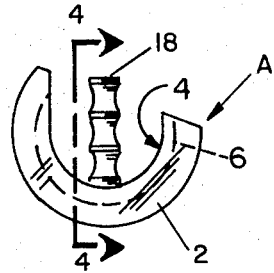
FIGS. 2 and 3 are, respectively, side and frontal views of the humeral component.
Figure 3:
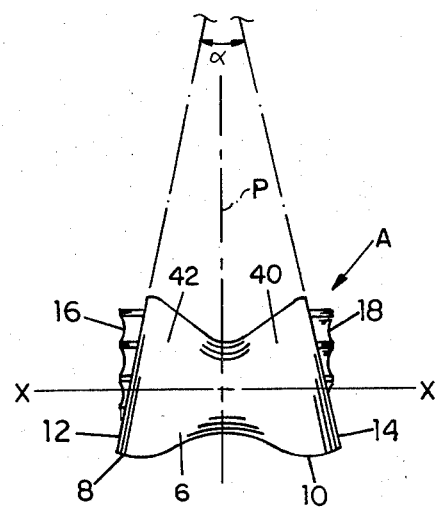
Figure 4:
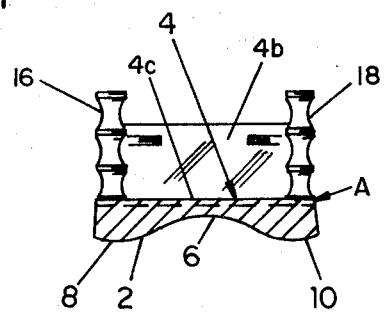
FIG. 4 is a transverse sectional view taken on line 4—4 of FIG. 2.
Figure 5:
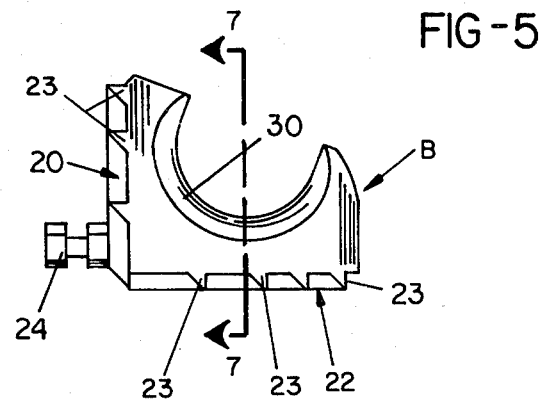
FIGS. 5, 6 and 7 are side, top and sectional views, respectively, of the ulnar component, the sectional view being taken along the line 7—7 of FIG. 5.

The endoprosthetic elbow joint device provided by the invention is of the hingeless type and comprises a humeral component A and an ulnar component B which have complementary, cooperative, bearing surfaces. The surfaces are in rotatably sliding contact after implantation and have complex interfitting transverse configurations which cause the bearing surfaces to interfit each with the other to provide improved transverse or lateral stability of the elbow joint, and improved resistance to compressive loading perpendicular to the longitudinal axis of the elbow joint.

The humeral component A of the prosthesis is particularly shown in FIGS. 1-4 and takes the form of an externally arcuate device whose external surface 2 extends through an arc of in excess of 180° and, preferably, approximately 200°. External surface 2 of the humeral component A forms a circumferentially convex external bearing surface. Humeral component A is provided with a longitudinally concave internal fixation surface 4, both surfaces 2 and 4 being preferably formed on the arc of the same circle throughout a substantial part of the length of the component A. The external bearing surface 2 extends across the entire arcuate length of the component A and has a uniform complex transverse configuration throughout its length which at every transverse section comprises a longitudinally extending centrally located concave groove 6 of curved transverse configuration on each side of which there is a longitudinally extending convex ridge, these ridges being denoted at 8, 10. The fixation surface 4 presents anterior, posterior, and distal surfaces 4a, 4b and 4c for fixation to the distal end of the humerus. The lateral and medial end walls of the humeral component A are designated by numerals 12, 14, respectively, the lateral end wall 12 forming an additional planar fixation surface. The medial end wall 14 is not a fixation surface. End walls 12 and 14 converge proximally and posteriorly for better anatomical fit. The preferred included angle of convergence $\alpha$, of the proximally tapering end walls 12, 14, (see FIG. 3) is between about 14°–20°. Serrated fixation posts 16, 18 extend inwardly and upwardly from the fixation surface 4c for driving attachment into the humerus in a longitudinal direction for increased security of the implant. The internal fixation surfaces 4a, 4b, and 4c, and posts 16, 18 are affixed to the distal end of the humerus, by means of an appropriate cement, such as methyl methacrylate.

Figure 6:
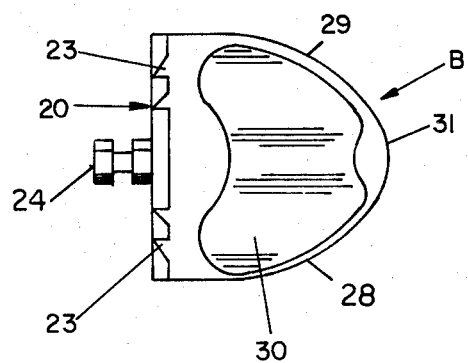
Figure 7:
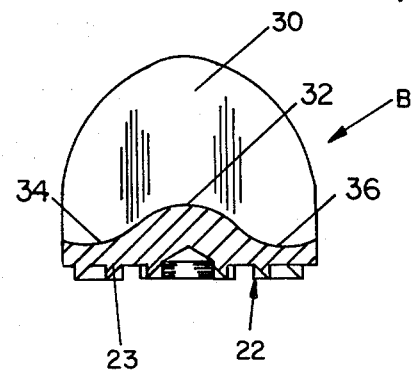

The ulnar component B is particularly illustrated in FIGS. 1 and 5–7 and comprises fixation surfaces 20, 22 which are disposed, preferably, at right angles to each other, as viewed laterally, for reception in a correspondingly shaped resected area at the proximal end of the ulna, and which are externally provided with ridges 23 having sharp edges for providing additional security to the prosthesis when in place. A fixation post 24 extends normal to fixation surface 20 for driving implantation longitudinally of the ulna. In plan view as shown in FIG. 6, the ulnar component preferably follows the shape of the proximal end of the ulna and therefore has curved medial and lateral side edges 28, 29 which converge toward the posterior tip 31 of the ulnar component B. The ulnar component also comprises an internal bearing surface denoted generally at 30 which is arcuately concave in shape, as viewed laterally, and extends through approximately 175°–180° of arc. The transverse configuration of this bearing surface (i.e., as viewed anteriorly) is particularly shown in FIG. 7 of the drawings and comprises a centrally located longitudinally extending convex ridge 32 of curved transverse configuration on the two sides of which there are concave longitudinally extending grooves 34, 36. The convex ridge 32 and both concave grooves 34, 36 extend throughout substantially the entire width and length of the bearing surface of the ulnar component B and the transverse configuration is uniform throughout such length.

The surface of the centrally located groove 6 of the humeral component A and the surface of the centrally located ridge 32 of the ulnar component B are arcs of substantially the same circle and the surfaces of the convex ridges 8, 10 of the humeral component and the surfaces of the grooves 34, 36 of the ulnar component are arcs of substantially the same circle which is of greater radius than that of the centrally located ridge and groove, 6 and 32, respectively.

The humeral component A is preferably made of a biologically inert metallic material such as chromecobalt alloy or stainless steel, and the ulnar component is preferably made of a biologically inert synthetic plastic material such as high density polyethylene. The resulting bearing surface between the components has a low coefficient of friction.

The surgical procedure for implanting the endoprosthesis of this invention will now be described:

1. The operation is performed with the patient in the lateral decubitus position with the upper extremity draped over a rest.
2. With a sterile tourniquet inflated about the brachium a 12 cm. posterior, longitudinal incision is made which is centered on, and slightly lateral to, the olecranon process.
3. Through this incision, the deep fascia is longitudinally incised.
4. The ulnar nerve is isolated in the proximal aspect of the wound and mobilized distally into the substance of flexor carpi ulnaris muscle. The nerve is retracted medially with a Penrose drain.
5. A unique W-shaped incision is made through the tendinous insertion of triceps. The medial arm of the W defines the medial border of triceps; the lateral border of the W defines the interval between the lateral border of triceps and the anconeous. The central portion of the W is based on the olecranon and comes to a point 4 cm. proximal to the joint line. The transected triceps is retracted proximally.
6. The origin of anconeus muscle and the underlying lateral collateral ligament are mobilized as a unit from the lateral epicondyle and retracted to expose the radial head.
7. The radial neck is transected and the head is removed.
8. The posterior, fan-like portion of the medial collateral ligament is mobilized from its insertion on the ulna.
9. The elbow is dislocated by displacing the humerus posteriorly and placing the elbow in excessive valgus.
10. A humeral cutting guide of appropriate size is positioned on the distal humerus by placing the center of the guide in the trochlear sulcus and aligning the handle with the long axis of the humerus. The medial margin of the appropriate size cutting guide will line up with the medial margin of the trochlea. The guide is secured by passing two drills through the guide into the distal humerus. The anterior and posterior surfaces of the trochlea are trimmed in line with the anterior and posterior surfaces of the cutting guide. The guide is removed.

11. The distal surface of the humerus is trimmed with the use of a second cutting guide.

12. A trial fitting of the appropriate size humeral component is performed. If position and alignment are adequate, attention is turned to the ulna.

13. Two right angle osteotomies are made to trim the articular surface of the proximal ulna. These osteotomies start at the tip of the coronoid and olecranon processes and are perpendicular to the plane defined by the semicircular crest on the articular surface of the proximal ulna.

14. Currette holes are made on these osteotomy surfaces to increase cement fixation. A small opening is made distally to accommodate the stud on the ulnar component.

15. A trial reduction of both components is performed and the elbow carried through a full range of motion.

16. A mix of methyl methacrylate is prepared and the humeral and ulnar components are cemented in place. Excess cement is removed during polymerization.

17. The tourniquet is deflated and hemostasis obtained.

18. The origin of anconeus with the underlying lateral collateral ligament is reattached to the lateral epicondyle through a drill hole in bone. The posterior portion of the medial collateral ligament is repaired with interrupted non-absorbable sutures.

19. The triceps tendon is reapproximated with interrupted, nonabsorbable sutures.

20. A hemovac drain is left in the elbow joint and brought through the skin proximally.

21. The deep fascia and skin are closed in separate layers.

22. A long arm bulky compression dressing and a posterior plaster splint are applied.

It is to be noted that the outer bearing surface 2 of the humeral component A is designed with a medial side 40 (shown in FIG. 3 as that half of the component A to the right of the transverse axial plane P) that re-duplicates the medial facet of the normal trochlea. In order to impart stability on the lateral side once the radial head has been excised, the humeral component A is made with a lateral facet 42 that is a mirror image of the medial facet and thus differs from the normal trochlea. This design increases the total articular surface area of the prosthesis by resurfacing approximately one-third of the capitellum in addition to the entire trochlea and it also eliminates the need for right and left prostheses. The humeral component has a single axis of rotation along the longitudinal axis "X" (see FIG. 3) and the end surfaces 12, 14 are tapered both proximally, as well posteriorly to better conform to the normal anatomy.

It is also to be noted that fixation of the humeral component is provided on the anterior, distal and posterior surfaces 4a, 4c and 4b as the distal end of the humerus seats into a slot defined by fixation surface 4 of the humeral component A. Additional fixation is provided by the two fixation pegs—in the base of this groove. This fixation design gives particular resistance to torque as fixation is distributed well away from the central axis of the humerus. The humeral component is preferably made in several lengths to accommodate varying distal humeral sizes.

In the application and use of the complete prosthesis, after implantation of the components their bearing surfaces will be in sliding engagement permitting relative rotational sliding movement between the humerus and ulna. The cooperating, complementary transverse configuration of the two bearing surfaces will cause the two components to closely interfit along their entire cooperating complementary surfaces. The interfitting grooves and ridges will prevent undesired transverse movement of the humerus and ulna while at the same time permitting side to side movement under varus-valgus stress because of the presence of the centrally located concave grooves 6 of the convex ridge 32 of the ulnar component. In addition, the outer convex ridges 8, 10 of the humeral component, together with complementary concave grooves 34, 36 present generally confronting surfaces providing resistance to perpendicularly oriented compressive axial loading forces on the elbow joint, as when a person walks on crutches, or pushes away from a chair.

In more precise geometric terms the device of this invention may be described as having (a) a humeral component A comprising an inner fixation surface 4 defining a longitudinally extending slot relative to a longitudinal axis "X" passing therethrough and an external sellar-shaped bearing surface (2) defined by a longitudinally extending convex arcuate segment of greater than 180° extent, and preferably of about 200°–220° extent (as viewed laterally), the radius of curvature through any section of convex arcuate segment defining each of the lateral ends (8, 10) of said bearing surface being of greater radius than the radius of curvature through an axial plane (P) taken perpendicular to said longitudinal axis "X" of said bearing surface, and the radius of curvature of said convex arcuate segment defining said bearing surface gradually increasing from the central axial plane P laterally outwardly to said lateral ends, and said outer sellar-shaped bearing surface being further defined by a transverse convex curvature at each of the lateral ends thereof faring smoothly into a transverse concave curvature (6) formed between said lateral ends; and (b) an ulnar component B having an inner sellar-shaped bearing surface (30) that is generally complementary with a major portion of said outer sellar-shaped bearing surface (2) of said humeral component A, and an outer fixation surface means (20, 22), whereby said complementary sellar-shaped bearing surfaces permit stable multi-directional movement of said humeral and ulnar components with respect to each other. The clinical trials with seven patients utilizing the endoprosthesis of this invention have been completed with follow-up varying from six (6) months to over a year. All seven patients have had longstanding rheumatoid arthritis and all seven have had several bilateral elbow involvement. There have been no complications related to these procedures. All wounds have healed per primum, there have been no infections, and no nerve palsies. All seven elbows are normally aligned and completely stable. Five of seven patients use supportive devices in both upper extremities to ambulate. Elbow motion was increased:

| PREOP. MOTION | POSTOP. MOTION |
|---|---|
| 45°–130° | 25°–150° |
| 55°–130° | 10°–135° |
| 75°–90° | 30°–135° |
| 70°–85° | 25°–130° |
| 45°–115° | 30°–130° |
| 50°–80° | 30°–125° |
| 50°–130° | 15°–135° |

|  | PREOP. MOTION | POSTOP. MOTION |
| --- | --- | --- |
| Mean | 55°–110° | 23°–134° |
| Mean Range | 55° | 115° |

The form of elbow joint endoprosthesis herein described may also be applied as an endoprosthesis for knee, wrist, and ankle joints of the human body. Other modifications and applications of this invention will become apparent to those skilled in the art. Hence, I intend to be bound only by the claims which follow.

I claim:

1. An endoprosthetic joint device comprising:
  (a). a first component
    i. Which is longitudinally arcuate in configuration,
    ii. having an internal longitudinally concave fixation surface adapted for implantation in one bone of a joint of the body, and
    iii. an external longitudinally convex bearing surface which extends through at least 180° of arc and has a similar transverse configuration from end to end comprising a centrally located concave groove of curved transverse configuration extending longitudinally substantially from end to end of the bearing surface and a convexly curved ridge at each side of the concave groove extending longitudinally substantially from end to end of the groove, and
  (b). a second component having
    i. two external fixation surfaces which are at a right angle to each other and are constructed and adapted for implantation and fixation in a second bone of a joint of a body, and
    ii. an internal arcuate bearing surface which is longitudinally concave and extends through at least 175° of arc and has a similar transverse configuration from end to end comprising a centrally located convexly curved ridge extending longitudinally substantially from end to end of the bearing surface and a concave groove of curved transverse configuration at each side of the ridge extending longitudinally substantially from end to end thereof,
  (c). the surface of the ridge of the second component being curved transversely at each point along its length on an arc substantially the same as the transverse curvature of the concave groove of the first component at each corresponding point of engagement,
  (d). the surfaces of the concave grooves of the second component being curved at each point along its length transversely on arcs substantially the same as the transverse curvatures of the convex ridges of the first component at each corresponding point of engagement, and
  (e). lateral end walls which converge proximally and posteriorly whereby the bearing surfaces of the two components taper uniformly from one end to the other.

2. As a new article of manufacture, a component of an endoprosthetic joint device, said component being of arcuate shape and having an external arcuate bearing surface and an internal arcuate fixation surface adapted for implantation and fixation in the end of a bone of a joint of the body, the bearing surface tapering from end to end and being longitudinally convex and having similar transverse configuration from end to end comprising a centrally located concave groove of curved transverse configuration extending from end to end of the bearing surface and a convexly curved ridge at each side of the concave groove extending throughout the longitudinal extent of the bearing surface.

3. As a new article of manufacture, a component of an endoprosthetic joint device, said component having two external fixation surfaces positioned at approximately a right angle to each other, and an arcuate longitudinally concave internal bearing surface having similar transverse configuration from end to end comprising a centrally located convexly curved ridge extending longitudinally substantially from end to end of the bearing surface and a concave groove of curved transverse configuration extending from end to end of the bearing surface on each side of the ridge.

4. As a new article of manufacture, a component of an endoprosthetic joint device, said component being of arcuate shape and having an external arcuate bearing surface and an internal arcuate fixation surface adapted for implantation and fixation in the end of a bone of a joint of the body, the bearing surface being longitudinally convex and having similar transverse configuration from end to end, comprising a centrally located concave groove of curved transverse configuration extending from end to end of the bearing surface and a convexly curved ridge at each side of the concave groove extending throughout the longitudinal extent of the bearing surface, and lateral end walls which converge proximally and posteriorly.

5. As a new article of manufacture, a component of an endoprosthetic joint device, said component having two external fixation surfaces positioned at approximately a right angle to each other, and an arcuate longitudinally concave internal bearing surface having similar transverse configuration from end to end comprising a centrally located convexly curved ridge extending longitudinally substantially from end to end of the bearing surface and a concave groove of curved transverse configuration extending from end to end of the bearing surface on each side of the ridge, the component when viewed in the superior or inferior aspect tapering medially laterally toward the posterior.

* * * * *